United States Patent [19]

Absil et al.

[11] Patent Number: 5,030,787

[45] Date of Patent: * Jul. 9, 1991

[54] CATALYTIC DISPROPORTIONATION/TRANSALKYLATION UTILIZING A C9+ AROMATICS FEED

[75] Inventors: Robert P. L. Absil, West Deptford; Scott Han, Lawrenceville; David O. Marler, Deptford; David S. Shihabi, Pennington, all of N.J.; James C. Vartuli, West Chester, Pa.; Philip Varghese, Villa Della Rosa, Singapore

[73] Assignee: Mobil Oil Corp., Fairfax, Va.

[*] Notice: The portion of the term of this patent subsequent to Jan. 1, 2008 has been disclaimed.

[21] Appl. No.: 511,145

[22] Filed: Apr. 19, 1990

Related U.S. Application Data

[63] Continuation-in-part of Ser. No. 469,645, Jan. 24, 1990, abandoned, which is a continuation-in-part of Ser. No. 252,524, Oct. 6, 1988, Pat. No. 4,954,325, which is a continuation-in-part of Ser. No. 98,176, Sep. 18, 1987, abandoned, which is a continuation-in-part of Ser. No. 890,268, Jul. 29, 1986, abandoned.

[51] Int. Cl.$^5$ .................................................. C07C 2/66
[52] U.S. Cl. ................................................................. 585/475
[58] Field of Search .......................................... 585/475

[56] References Cited

U.S. PATENT DOCUMENTS

| | | | |
|---|---|---|---|
| Re. 27,639 | 5/1973 | Thomas et al. | |
| Re. 31,781 | 12/1984 | Dwyer | |
| 3,002,698 | 10/1961 | Gallo | |
| 3,065,209 | 6/1976 | Butter et al. | |
| 3,126,422 | 3/1964 | Planchard, Jr. | |
| 3,413,374 | 11/1968 | Sato et al. | |
| 3,551,509 | 12/1970 | Thomas et al. | |
| 3,598,878 | 8/1971 | Kovach et al. | |
| 3,598,879 | 8/1971 | Kmecak et al. | |
| 3,607,961 | 9/1971 | Kovach et al. | |
| 3,848,009 | 11/1974 | Wadley et al. | 260/668 FA |
| 3,886,223 | 5/1975 | Kemme et al. | 260/668 |
| 3,962,364 | 6/1976 | Young | |
| 3,965,207 | 6/1976 | Weinstein | |
| 3,965,208 | 6/1976 | Butter et al. | |
| 4,001,346 | 1/1977 | Chu | |
| 4,007,231 | 2/1977 | Butter | |
| 4,011,276 | 3/1977 | Chu | |
| 4,016,218 | 4/1977 | Haag et al. | |
| 4,016,219 | 4/1977 | Kaeding | |
| 4,026,959 | 5/1977 | Kemme et al. | 260/668 |
| 4,029,716 | 6/1977 | Kaeding | |
| 4,041,089 | 8/1977 | Allen et al. | 260/668 |
| 4,052,476 | 10/1977 | Morrison | |
| 4,067,920 | 1/1978 | Kaeding | |
| 4,100,215 | 7/1978 | Chen | |
| 4,101,595 | 7/1978 | Chen et al. | |
| 4,101,597 | 7/1978 | Breckenridge | |
| 4,117,026 | 9/1978 | Haag et al. | |
| 4,127,616 | 11/1978 | Rodewald | |
| 4,152,363 | 5/1979 | Tabak et al. | |
| 4,152,364 | 5/1979 | Chu | |
| 4,158,676 | 6/1979 | Smith et al. | |
| 4,159,282 | 6/1979 | Olson et al. | |
| 4,159,283 | 6/1979 | Nicoletti et al. | |
| 4,163,028 | 7/1979 | Tabak et al. | |
| 4,188,282 | 2/1980 | Tabak et al. | |
| 4,224,141 | 9/1980 | Morrison et al. | |
| 4,351,979 | 9/1982 | Chester et al. | |
| 4,361,713 | 11/1982 | Kaeding | |
| 4,365,104 | 12/1982 | Kaeding | |
| 4,367,359 | 1/1983 | Kaeding | |
| 4,370,508 | 1/1983 | Kaeding | |
| 4,380,685 | 4/1983 | Chu | |
| 4,384,155 | 5/1983 | Chu | |
| 4,418,235 | 11/1983 | Haag et al. | 585/407 |
| 4,439,409 | 3/1984 | Puppe et al. | |
| 4,826,667 | 5/1989 | Zones et al. | |
| 4,891,458 | 1/1990 | Innes et al. | 585/323 |
| 4,982,040 | 1/1991 | Angevine et al. | 585/475 |

FOREIGN PATENT DOCUMENTS

0231860 8/1987 European Pat. Off.
0293032 11/1988 European Pat. Off.

*Primary Examiner*—Anthony Mc Farlane
*Attorney, Agent, or Firm*—Alexander J. McKillop; Charles J. Speciale; Dennis P. Santini

[57] ABSTRACT

A feedstock containing one or more C9+ aromatic compounds, and optionally benzene and/or toluene, undergoes conversion over a catalyst comprising a zeolite possessing a Constraint Index of from 1 to about 3 to provide a product containing a substantial amount of $C_6$–$C_8$ aromatic compounds, e.g. benzene and xylene(s), predominantly the latter.

16 Claims, No Drawings

CATALYTIC DISPROPORTIONATION/TRANSALKYLATION UTILIZING A C9+ AROMATICS FEED

CROSS-REFERENCE TO RELATED APPLICATIONS

This application is a continuation-in-part of U.S. patent application Ser. No. 469,645, filed Jan. 24, 1990, now abandoned, which is a continuation-in-part of U.S. patent application Ser. No. 254,524, filed Oct. 6, 1988, now U.S. Pat. No. 4,954,325, which is a continuation-in-part of U.S. patent application Ser. No. 98,176, filed Sept. 18, 1987, now abandoned, which is a continuation-in-part of U.S. patent application Ser. No. 890,268, filed Jul. 29, 1986, now abandoned.

BACKGROUND OF THE INVENTION

This invention is directed to an improved process for the catalytic conversion of a C9+ aromatic feedstock, optionally containing toluene, in the presence of a certain class of zeolite catalysts under transalkylation/disproportionation reaction conditions to provide a product containing significant amounts of benzene and xylene(s). When compared with other disproportionation/transalkylation processes, the present process provides significant improvement in product xylene/benzene mole ratio.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties. Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1:2. The electrovalence of the tetrahedra containing the Group IIIA element, e.g., aluminum, is balanced by the inclusion in the crystal of a cation, e.g., an alkali metal or an alkaline earth metal cation. This can be expressed wherein the ratio of the Group IIA element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation.

Prior art techniques have resulted in the formation of a great variety of synthetic zeolites. Many of these zeolites have come to be designated by letter or other convenient symbols, as illustrated by zeolite Z (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); zeolite ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (U.S. Pat. No. Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724, 4,073,865 and 4,104,294 describe crystalline silicates of varying alumina and metal content.

U.S. Pat. No. 4,380,685 discloses the para-selective alkylation, transalkylation or disproportionation of a substituted aromatic compound to provide a mixture of dialkylbenzene compounds employing as catalyst a zeolite characterized by a Constraint Index of 1 to 12 and a silica/alumina mole ratio of at least 12/1, the catalyst having incorporated thereon various metals and phosphorus. Other patents covering alkylation and transalkylation processes include U.S. Pat. Nos. 4,127,616; 4,361,713, 4,365,104; 4,367,359; 4,370,508; and, 4,384,155. Toluene is converted to para-xylene as disclosed in U.S. Pat. Nos. 3,965,207; 3,965,208; 3,965,209; 4,001,346; 3,002,698; 4,067,920; 4,100,215; and, 4,152,364, to name a few. Alkylation with olefins is disclosed, for example, in U.S. Pat. Nos. 3,962,364 and 4,016,218. Toluene shown to be is disproportionated in, for example, U.S. Pat. Nos. 4,052,476; 4,007,231; 4,011,276; 4,016,219; and, 4,029,716. Isomerization of xylenes is disclosed in, for example, U.S. Pat. Nos. 4,101,595; 4,158,676; 4,159,282; 4,351,979; 4,101,597; 4,159,283; 4,152,363; 4,163,028; 4,188,282; and, 4,224,141.

U.S. Pat. No. 3,551,509 and U.S. Pat. No. Re. 27,639 disclose transalkylation between trimethylbenzenes and toluene to yield xylenes and benzene in the presence of a crystalline aluminosilicate catalyst having large pore openings of 8 to 15 Angstrom units and preferably containing Group VIII metals, hydrogen and rare earth cations.

U.S. Pat. Nos. 3,126,422; 3,413,374; 3,598,878; 3,598,879; and, 3,607,961 describe the vapor-phase disproportionation of toluene over various catalysts. U.S. Pat. No. 4,117,026 discloses disproportionation of toluene over a catalyst comprising a zeolite having a silica/alumina mole ratio of at least 12, a Constrain Index of 1 to 12 and a specified sorption capacity for xylenes.

U.S. Pat. No. Re. 31,781 (of original U.S. Pat. No. 4,100,214) discloses the use of from 3 to 30 combined weight percent of toluene and C9+ recycle material as diluents with a monocyclic alkyl aromatic hydrocarbon feed selected from the xylenes, mesitylene, durene, hemimellitene, pseudocumene, prehnitene, isodurene and 1,3,5-triethylbenzene for the vapor-phase isomerization of said feed employing as catalyst, a zeolite having a Constrain Index of 1 to 12, e.g., ZSM-5, ZSM-11, ZSM-12, ZSM-35 and ZSM-38.

SUMMARY OF THE INVENTION

This invention provides an improved process for the vapor-phase conversion of a feedstock containing at least one $C_9+$ aromatic compound to a product containing substantial quantities of $C_6$-$C_8$ compounds, e.g. benzene and xylene(s), predominantly the latter, which comprises contacting said feedstock containing $C_9+$ aromatic compound(s) and, optionally, benzene and/or toluene, with a conversion catalyst under vapor-phase conditions which effect the conversion of said feedstock to said product, the conversion catalyst comprising a zeolite possessing a Constraint Index, as hereinafter defined, of from 1 to about 3.

DESCRIPTION OF SPECIFIC EMBODIMENTS

The present invention relates to an improved disproportionation/transalkylation process. The improved process of this invention is conducted such that transalkylation of a $C_9+$ aromatics feedstock, or disproportionation of a feedstock containing toluene and $C_9+$ aromatic(s), is carried out in the vapor-phase by containing said feedstock in a reaction zone with a catalyst comprising a zeolite possessing a Constraint Index, as defined below, of from 1 to about 3 and preferably which has been hydrogen, hydrogen precursor and/or non-noble Group VIII metal exchanged, thermally treated and/or hydrothermally treated, under conditions effective to convert such feedstock to a product containing substantial quantities of $C_6$-$C_8$ aromatic compounds, e.g. benzene and xylene(s), especially the latter. The product effluent is separated and distilled to remove the desired products. If desired, any unreacted material(s), e.g., toluene and/or $C_9+$ compound(s), can be recycled.

The improvement of this invention resides in the product having higher xylene/benzene mole ratios than that obtainable with zeolite catalysts having a Constraint Index of greater than about 3, e.g., ZSM-5 which possesses a Constraint Index of 6–8.3 (when measured at 371° C.–316° C.). The product xylene/benzene mole ratios herein will generally be greater than about 0.80, usually greater than 0.90, and often greater than 1.

The $C_9+$ aromatics feed required for the process of this invention will comprise one or more aromatic compounds containing at least 9 carbons such as, e.g., trimethylbenzenes, dimethylethylbenzenes and diethylbenzenes, etc. Specific $C_9+$ aromatic compounds include mesitylene (1,3,5-trimethylbenzene), durene (1,2,4,5-trimethylbenzene), hemimellitene (1,2,3-trimethylbenzene), pseudocumene (1,2,4-trimethylbenzene), prehnitene (1,2,3,4-tetramethylbenzene), isodurene (1,2,3,4-tetramethylbenzene), and 1,3,5-triethylbenzene.

The feedstock employed in the present process conveniently contains benzene or, more preferably, toluene, in addition to the $C_9+$ compounds. The optional toluene charge is preferably dried in a manner which will minimize the water entering the reaction. Means known in the art suitable for drying toluene are numerous, including percolation through silica gel, activated alumina, molecular sieves or other suitable substances or the use of liquid charge dryers.

When toluene and/or benzene is additionally present in the feedstock, the $C_9+$ aromatics will ordinarily constitute at least about 3 wt. % of the total feed (the balance being toluene and/or benzene) and advantageously can comprise up to about 70 wt. % of the mixed feedstock. Of course, $C_9+$ aromatics can represent 100% of the feedstock for conversion in accordance with the present invention.

The toluene, when present in the feed, is disproportionated to aromatic concentrates of high value, e.g., xylene(s) and benzene, with the more valuable xylene(s) being the predominant product(s).

The improved selectivity of the process of the invention to xylene(s) is demonstrated by unexpectedly increased xylene(s)/benzene product mole ratios. This process can be conducted in either batch or fluid bed operation with the attendant benefits of either operation being readily obtainable.

In carrying out the process of the invention, the $C_9+$ aromatics feed, e.g., a recycle stream, is heated to a temperature within the range of from about 600° F. to about 1100° F. at a pressure within the range of from about atmospheric to about 1000 psig. Preferred inlet temperatures for the process of the present invention fall within the range of from about 650° F. to about 1000° F. and preferred pressures fall within the range of from about 50 psig to about 1000 psig. The hydrogen to hydrocarbon mole ratio can be from 0 (no added hydrogen) to about 10 with a preferred range of from 0 to about 3. A particularly preferred range of hydrogen to hydrocarbon mole ratio will be from 0 to about 2.

As mentioned above, the zeolite catalysts which are useful in the process of this invention are those possessing a Constraint Index of from 1 to about 3, and preferably not greater than about 2.5.

The method by which Constraint Index is determined is described fully in U.S. Pat. No. 4,016,218, incorporated herein by reference for details of the method.

Constraint Index (CI) values for some typical zeolites including some which are suitable as catalysts in the process of this invention are:

|  | CI (at test temperature) |
| --- | --- |
| ZSM-4 | 0.5 (316° C.) |
| ZSM-5 | 6–8.3 (371° C.–316° C.) |
| ZSM-11 | 5–8.7 (371° C.–316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-48 | 3.5 (538° C.) |
| ZSM-50 | 2.1 (427° C.) |
| MCM-22 | 1.5 (454° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6–2.0 (316° C.–399° C.) |

The above-described Constraint Index is an important and even critical definition of those zeolites which are useful in the instant invention. The very nature of this parameter and the recited technique by which it is determined, however, admits of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g., temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites but that such are the cumulative result of several variables useful in the determination and calculation thereof. Thus, for a given zeolite exhibiting a CI value within the range of 3 or less, depending on the temperature employed during the test method within the range of 290° C. to about 538° C., with accompanying conversion between 10% and 60%, the CI may vary within the indicated range of 3 or less. Accordingly, it will be understood to those skilled in the art that the CI as utilized herein, while affording a highly useful means for characterizing the zeolites of interest, is approximate taking into consideration the manner of its determination with the possibility in some instances of compounding variable extremes. However, in all instances, at a temperature within the above-specified range of 290° C. to about 538° C., the CI will have a value for any given zeolite of interest herein of not greater than about 3 and preferably not greater than about 2.5.

Some zeolite catalysts which are especially useful in the process of this invention include zeolites MCM-22, ZSM-12 and Beta.

ZSM-12 is more particularly described in U.S. Pat. No. 3,832,449, the entire contents of which are incorporated by reference herein.

Zeolite Beta is more particularly described in U.S. Pat. No. Re. 28,341 (of original U.S. Pat. No. 3,308,069), the entire contents of which are incorporated by reference herein.

Zeolite MCM-22, or simply "MCM-22", appears to be related to the composition named "PSH-3" described in U.S. Pat. No. 4,439,409. Zeolite MCM-22 does not appear to contain all the components apparently present in the PSH-3 compositions. Zeolite MCM-22 is not contaminated with other crystal structures, such as ZSM-12 or ZSM-5, and exhibits unusual sorption capacities and unique catalytic utility when compared to the PSH-3 compositions synthesized in accordance with U.S. Pat. No. 4,439,409.

Zeolite MCM-22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

wherein R is an organic component. The Na and R components are associated with the zeolite as a result of their presence during crystallization, and are easily removed by post-crystallization methods hereinafter more particularly described.

Zeolite MCM-22 is thermally stable and exhibits high surface area greater than 400 m²/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations. It and the other useful zeolite can be used as catalysts with acid activity without an exchange step. To the extent desired, however, the original sodium cations of the as-synthesized zeolite catalysts can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the catalytic activity for transalkylation/disproportionation. These include hydrogen, rare earth metals and metals of Groups IIA, IIIA, IVA, IB, IIB, IIIB, IVB and VIII of the Periodic Table of the Elements.

In its calcined form, zeolite MCM-22 appears to be made up of a single crystal phase with little or no detectable impurity crystal phases and has an X-ray diffraction pattern including the lines listed in Table I below:

TABLE I

| Interplanar d-Spacing (A) | Relative Intensity, I/Io × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an X-ray diffraction pattern including the following lines:

TABLE II

| Interplanar d-Spacing (A) | Relative Intensity, I/Io × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |

TABLE II-continued

| Interplanar d-Spacing (A) | Relative Intensity, I/Io × 100 |
|---|---|
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ is the intensity of the strongest line or peak, and d (obs.) the interplanar spacing in Angstroms Units (A), corresponding to the recorded lines, were determined. In Tables I and II, the relative intensities are given in terms of the symbols W=weak, M=medium, S=strong and VS=very strong. In terms of intensities, these may be generally designated as follows:

W = 0–20
M = 20–40
S = 40–60
VS = 60–100

It should be understood that these X-ray diffraction patterns are characteristic of all species of zeolite MCM-22. The sodium form as well as other cationic forms of this zeolite reveal substantially the same pattern with some minor shifts in interplanar spacing and variation in relative intensity. Other minor variations can occur depending on the Y to X, e.g., silicon to aluminum, mole ratio of the particular sample, as well as its degree of thermal treatment.

Zeolite MCM-22 can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
|---|---|---|
| $YO_2/X_2O_3$ | 10–60 | 10–40 |
| $H_2O/YO_2$ | 5–100 | 10–50 |
| $OH^-/YO_2$ | 0.01–1.0 | 0.1–0.5 |
| $M/YO_2$ | 0.01–2.0 | 0.1–1.0 |
| $R/YO_2$ | 0.05–1.0 | 0.1–0.5 |

In a preferred method of synthesizing zeolite MCM-22, the $YO_2$ reactant contains a substantial amount of solid $YO_2$, e.g., at least about 30 wt. % solid $YO_2$. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystal formation from the above mixture and is a distinct improvement over the synthesis method disclosed in U.S. Pat. No. 4,439,409. If another source of oxide of silicon, e.g., Q-Brand (a sodium silicate comprised of about 28.8 wt. % of $SiO_2$, 8.9 wt. % $Na_2O$ and 62.3 wt. % $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt. % solid $YO_2$, e.g., silica, and preferably at least about 40 wt. % solid $YO_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals (based on total weight) of the crystalline product.

The zeolite conversion catalysts herein can be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be introduced in the catalyst composition by way of co-crystallization, exchanged into the composition to the extent a Group IIIA element, e.g., aluminum, is in the structure, impregnated therein or intimately physically admixed therewith. Such component can be impregnated in, or on, the zeolite such as, for example, by, in the case of platinum, treating the zeolite with a solution containing a platinum metal-containing ion. Thus, suitable platinum compounds for this purpose include chloroplatinic acid, platinous chloride and various compounds containing the platinum amine complex.

The zeolite catalysts, especially in their metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to their use in the process of this invention, the zeolite crystals should be dehydrated, at least partially. This can be done by heating the crystals to a temperature in the range of from about 200° C. to about 595° C. in an inert atmosphere, such as air, nitrogen, etc. and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

The zeolite catalysts employed herein can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

It may be desired to incorporate the selected zeolite catalyst with another material which is resistant to the temperatures and other conditions employed in the process of this invention. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the catalyst zeolite, i.e., combined therewith or present during its synthesis, which itself is catalytically active may change the conversion and/or selectivity of the catalyst. Inactive materials suitably serve as diluents to control the amount of conversion so that transalkylated/disproportionated products can be obtained economically and orderly without employing other means for controlling the rate of reaction. These materials may be incorporated into naturally occurring clays, e.g., bentonite and kaolin, to improve the crush strength of the catalyst under commercial alkylation operating conditions. Said materials, i.e., clays, oxides, etc., function as binders for the catalyst. It is desirable to provide a catalyst having good crush strength because in commercial use, it is desirable to prevent the catalyst from breaking down into powder-like materials. These clay binders have been employed normally only for the purpose of improving the crush strength of the catalyst.

Naturally occurring clays which can be composited with the zeolite catalyst herein include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with zeolite also include inorganic oxides, notably alumina.

In addition to the foregoing materials, the zeolite catalyst can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia. It may also be advantageous to provide at least a part of the foregoing matrix materials in colloidal form so as to facilitate extrusion of the bound catalyst component(s).

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The stability of the zeolite catalyst may be increased by steaming, with suitable steam stabilization conditions including contacting the catalyst with, for example, 5–100% steam at a temperature of at least 300° C. (e.g. 300°–650° C.) for at least one hour (e.g. 1–200 hours) at a pressure of 100–2,500 kPa. In a more particular embodiment, the catalyst can be made to undergo steaming with 75–100% steam at 315°–500° C. and atmospheric pressure for 2–25 hours.

In order to more fully illustrate the transalkylation/disproportionation process of this invention and the manner of practicing same, the following examples are presented. In examples illustrative of the synthesis of zeolite, whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr of cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbent. Zeolite MCM-22 always exhibits Equilibrium Adsorption values of greater than about 10 wt. % for water vapor, greater than about 4.5 wt. %, usually greater than about 7 wt. % for cyclohexane vapor and greater than about 10 wt. % for n-hexane vapor. These vapor sorption capacities are a notable distinguishing feature of zeolite MCM-22.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant $=0.016$ sec $^{-1}$). The Alpha Test is described in U.S. Pat. No. 3,354,078, in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

One part of sodium aluminate (43.5% $Al_2O_3$, 32.2% $Na_2O$, 25.6% $H_2O$) was dissolved in a solution containing 1 part of 50% NaOH solution and 103.13 parts $H_2O$. To this was added 4.50 parts hexamethyleneimine. The resulting solution was added to 8.55 parts of Ultrasil, a precipitated, spray-dried silica (about 90% $SiO_2$).

The reaction mixture had the following composition, in mole ratios:

$SiO_2/Al_2O_3 = 30.0$
$OH^-/SiO_2 = 0.18$
$H_2O/SiO_2 = 44.9$
$Na/SiO_2 = 0.18$

R/SiO$_2$ = 0.35
where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table III proving the product to be MCM-22. The sorption capacities of the calcined material were measured to be:

H$_2$O: 15.2 wt. %
Cyclohexane: 14.6 wt. %
n-Hexane: 16.7 wt. %

The surface area of the calcined crystalline material was measured to be 494 m$^2$/g.

The chemical composition of the uncalcined material was determined to be as follows:

| Component | wt. % |
|---|---|
| SiO$_2$ | 66.9 |
| Al$_2$O$_3$ | 5.40 |
| Na | 0.03 |
| N | 2.27 |
| Ash | 76.3 |
| SiO$_2$/Al$_2$O$_3$, mole ratio = 21.1 | |

TABLE II

| Degrees 2-Theta | Interplanar d-Spacing (A) | I/I$_o$ |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLES 3-5

Three separate synthesis reaction mixtures were prepared with compositions indicated in Table IV. The mixtures were prepared with sodium aluminate, sodium hydroxide, Ultrasil, hexamethyleneimine (R) and water. The mixtures were maintained at 150° C., 143° C., respectively, for 7, 8 and 6 days respectively in stainless steel autoclaves at autogenous pressure. Solids were separated from any unreacted components by filtration and then water washed, followed by drying at 120° C. The product MCM-22 crystals were analyzed by X-ray diffraction, sorption, surface area and chemical analyses and the results are presented in Table IV. The sorption and surface area measurements were of the calcined product.

TABLE IV

| Example | 3 | 4 | 5 |
|---|---|---|---|
| Synthesis Mixture, mole ratios | | | |
| SiO$_2$/Al$_2$O$_3$ | 30.0 | 30.0 | 30.0 |
| OH$^-$/SiO$_2$ | 0.18 | 0.18 | 0.18 |
| H$_2$O/SiO$_2$ | 19.4 | 19.4 | 44.9 |
| Na/SiO$_2$ | 0.18 | 0.18 | 0.18 |
| R/SiO$_2$ | 0.35 | 0.35 | 0.35 |
| Product Composition, Wt. % | | | |
| SiO$_2$ | 64.3 | 68.5 | 74.5 |
| Al$_2$O$_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| SiO$_2$/Al$_2$O$_3$, mole ratio | 22.5 | 20.9 | 26.0 |
| Adsorption, Wt. % | | | |
| H$_2$O | 14.9 | 13.6 | 14.6 |
| Cyclohexane | 12.5 | 12.2 | 13.6 |
| n-Hexane | 14.6 | 16.2 | 19.0 |
| Surface Area, m$^2$/g | 481 | 492 | 487 |

EXAMPLE 6

Quantities of the calcined (538° C. for 3 hours) crystalline silicate MCM-22 products of Examples 3, 4 and 5 were tested in the Alpha Test and found to have Alpha Values of 227, 180 and 187, respectively.

EXAMPLE 7

To demonstrate a further preparation of MCM-22 zeolite, 4.49 parts of hexamethyleneimine was added to a solution containing 1 part of sodium aluminate, 1 part of 50% NaOH solution and 44.19 parts of H$_2$O. To the combined solution were added 8.54 parts of Ultrasil silica. The mixture was crystallized with agitation at 145° C. for 59 hours and the resultant product was water washed and dried at 120° C.

Product chemical composition, surface area and adsorption analyses results are set forth in Table V:

TABLE V

| Product Composition (uncalcined) | |
|---|---|
| C | 12.1 wt. % |
| N | 1.98 wt. % |
| Na | 640 ppm |
| Al$_2$O$_3$ | 5.0 wt. % |
| SiO$_2$ | 74.9 wt. % |
| SiO$_2$/Al$_2$O$_3$, mole ratio | 25.4 |
| Adsorption, wt. % | |
| Cyclohexane | 9.1 |
| N-Hexane | 14.9 |
| H$_2$O | 16.8 |
| Surface Area, m$^2$/g | 479 |

EXAMPLE 8

Twenty-five grams of solid crystal product from Example 7 were calcined in a flowing nitrogen atmospheres at 538° C. for 5 hours, followed by purging with 5% oxygen gas (balance N$_2$) for another 16 hours at 538° C.

Individual 3 g samples of the calcined material were ion-exchanged with 100 ml of 0.1N TEABr, TPABr and LaCl$_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| Exchange Ions Ionic Composition, wt. % | TEA | TPA | La |
|---|---|---|---|
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite had very good stability under severe hydrothermal treatment.

EXAMPLE 11

This example illustrates the preparation of MCM-22 zeolite where X in the general formula, supra, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:
$SiO_2/B_2O_3 = 6.1$
$OH^-/SiO_2 = 0.06$
$H_2O/SiO_2 = 19.0$
$K/SiO_2 = 0.06$
$R/SiO_2 = 0.30$
where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 540° C. and found to have the following sorption capacities:
$H_2O$ (12 Torr): 11.7 wt. %
Cyclohexane (40 Torr): 7.5 wt. %
n-Hexane (40 Torr): 11.4 wt. %
The surface area of the calcined crystalline material was measured (BET) to be 405 m²/g.

The chemical composition of the uncalcined material was determined to be as follows:
N: 1.94 wt. %
Na: 175 ppm
K: 0.60 wt. %
Boron: 1.04 wt. %
$Al_2O_3$: 920 ppm
$SiO_2$: 75.9 wt. %
Ash: 74.11 wt. %
$SiO_2/Al_2O_3$, molar ratio = 1406
$SiO_2/(Al+B)_2O_3$, molar ratio = 25.8

EXAMPLE 12

A portion of the calcined crystalline product of Example 11 was treated with $NH_4Cl$ and again calcined. The final crystalline product was tested in the Alpha Test and found to have an Alpha Value of 1.

EXAMPLE 13

This example illustrates another preparation of MCM-22 in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:
$SiO_2/B_2O_3 = 12.3$
$OH^-/SiO_2 = 0.056$
$H_2O/SiO_2 = 18.6$
$K/SiO_2 = 0.056$
$R/SiO_2 = 0.30$
where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:
$H_2O$: 14.4 wt. %
Cyclohexane: 4.6 wt. %
n-Hexane: 14.0 wt. %
The surface area of the calcined crystalline material was measured to be 438 m²/g.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio = 249 | |
| $SiO_2/(Al + B)_2O_3$, molar ratio = 28.2 | |

EXAMPLE 14

A portion of the calcined crystalline product of Example 13 was tested in the Alpha Test and found to have an Alpha Value of 5.

EXAMPLES 15 and 16

These examples illustrate the catalytic conversion of a mixture of toluene and a $C_9^+$ aromatics feed with a zeolite of Tables I-II (Example 15) and compare the performance of this zeolite with that of ZSM-5, i.e. a catalyst which is outside the scope of this invention (Example 16).

The zeolite of the invention was prepared by adding 4.49 parts hexamethyleneimine to a mixture containing 1.00 part sodium aluminate, 1.00 part 50% NaOH, 8.54 parts Ultrasil VN3 and 44.19 parts deionized $H_2O$. The reaction mixture was heated to 143° C. (290° F.) and stirred in an autoclave at that temperature for crystallization. After full crystallinity was achieved, the majority of the hexamethyleneimine was removed from the autoclave by controlled distillation and the zeolite crystals separated from the remaining liquid by filtration, washed with deionized $H_2O$ and dried. A 65 wt. % zeolite/35 wt. % Al$_2$O$_3$ catalyst composition was prepared from the zeolite by extrusion. The material was then dried overnight at 120° C. (250° F.), calcined at 480° C. (900° F.) for three hours in 3 v/v/min N$_2$, then treated with 50 vol. % air/50 vol. % N$_2$ at 3 v/v/min, also at 480° C. (900° F.) for one hour. The calcination was completed by raising the temperature to 540° C. (1000° F.) at 3° C. (5° F.)/min and finally switching to 100% air (3 v/v/min) and holding at this temperature for three hours. A similar process was used to prepare the ZSM-5 catalyst.

The properties of the zeolite catalyst compositions are set forth in Table VI as follows:

TABLE VI

|  | Zeolite of Invention | ZSM-5 |
|---|---|---|
| SiO$_2$/Al$_2$O$_3$, molar | 25 | 26 |
| Alpha Value | 215 | 423 |
| Sodium, ppm | 630 | 135 |
| Surface area, m$^2$/g | 451 | 325 |
| Real density, g/cc | 2.57 | 2.64 |
| Particle density, g/cc | 0.82 | 0.87 |
| Pore volume, cc/g | 0.83 | 0.77 |

The C$_9$+ aromatic feed had the composition set forth in Table VII as follows:

TABLE VII

|  | Wt. % | Mole % |
|---|---|---|
| Ethylbenzene | 0.02 | 0.02 |
| p-Xylene | 0.14 | 0.16 |
| o-Xylene | 0.36 | 0.41 |
| C$_9$ Aromatics | 83.29 | 84.60 |
| TMB (trimethylbenzene) | 39.05 | 39.66 |
| MEB (methylethylbenzene) | 37.38 | 37.97 |
| C$_{10}$ + Aromatics | 15.53 | 14.28 |
| DEB (dimethylethylbenzene) | 6.59 | 6.00 |
| DMEB | 4.51 | 4.10 |
| Total Xylenes | 0.50 | 0.58 |
| Total Aromatics | 99.34 | 99.49 |
| Total Non-Aromatics | 0.00 | 0.00 |

The total feed compositions are shown in Table VIII as follows:

TABLE VIII

| Total Feed Composition | | |
|---|---|---|
|  | Example 15 | Example 16 |
| Toluene | 67.45 | 66.86 |
| C$_9$+ | 31.84 | 31.88 |
| C$_9$- | 0.71 | 1.26 |

Each of the experiments was conducted in a stainless steel reactor having an external diameter of 1 cm at 4240 kPa (600 psig), 4 hr$^{-1}$ weight hourly space velocity (based on zeolite) and a hydrogen/hydrocarbon mole ratio of 2. The toluene was initially passed over the catalyst in each instance at a temperature required to maintain 48±1 wt. % toluene conversion.

Table IX below sets forth the reaction conditions and the product distributions:

TABLE IX

| Product Results | | |
|---|---|---|
|  | Example 15 | Example 16 |
| Conditions |  |  |
| Temperature$^1$, °F. | 885 | 750 |
| Toluene Conversion, wt. % | 48$^2$ | 48$^2$ |
| C$_9$ + Conversion, wt. % | 66 | 62 |
| Product Distribution |  |  |

TABLE IX-continued

| Product Results | | |
|---|---|---|
|  | Example 15 | Example 16 |
| C$_5$-, wt. % | 7.53 | 7.16 |
| Benzene | 16.94 | 19.86 |
| Toluene | 39.63 | 38.31 |
| Ethylbenzene | 1.37 | 1.34 |
| p-Xylene | 5.74 | 5.04 |
| m-Xylene | 12.26 | 10.93 |
| o-Xylene | 5.59 | 4.86 |
| Xylene/Benzene mole ratio | 1.02 | 0.77 |
| C$_9$+, wt. % | 10.94 | 12.50 |

$^1$Initial temperature required to maintain 48 ± 1 wt. % toluene conversion.
$^2$Initial toluene conversion which became 41 wt. % and 43 wt. %, respectively, in Examples 15 and 16 after C$_9$+ feed addition.

It is observed from these experiments that the present process, exemplified by Example 15, provides increased product xylene when compared to the experiment conducted with a similar feed but using ZSM-5 catalyst.

An additional benefit provided by the present process is the increased C$_9$+ conversion (Example 15:66 wt. % compared to Example 16:62 wt. %).

EXAMPLES 17 and 18

The process of Examples 15 and 16 was repeated with feed compositions shown in Table X below and with the weight hourly space velocity increased to 6 hr$^{-1}$. Product distributions from these experiments are presented in Table XI below:

TABLE X

|  | Example 17 | Example 18 |
|---|---|---|
| Toluene | 67.45 | 66.55 |
| C$_9$+ | 31.84 | 32.17 |
| C$_9$- | 0.71 | 1.28 |

TABLE XI

| Catalyst | Example 17 Zeolite of Invention | Example 18 ZSM-5 |
|---|---|---|
| Product Distribution |  |  |
| C$_5$-, wt. % | 5.53 | 6.09 |
| Benzene, wt. % | 15.71 | 18.51 |
| Toluene, wt. % | 41.90 | 39.61 |
| Ethylbenzene, wt. % | 1.66 | 1.40 |
| p-Xylene, wt. % | 5.45 | 4.97 |
| m-Xylene, wt. % | 11.55 | 10.61 |
| o-Xylene, wt. % | 5.31 | 4.62 |
| Xylene/Benzene mole ratio | 1.04 | 0.80 |
| C$_9$+, wt. % | 13.09 | 14.19 |

The results of Examples 17 and 18 again demonstrate the unexpected improvement of the present invention. The product mole ratio of xylene/benzene was 1.04 for Example 17 compared to only 0.80 for Example 18.

EXAMPLE 19

This example compares the performance of two zeolite Beta catalyst compositions for the conversion of a mixture of toluene and mesitylene with that of three ZSM-5 catalyst compositions.

The conversion conditions included a toluene to mesitylene mole ratio of 2:1, a hydrogen to hydrocarbon mole ratio of 1:1, a temperature of 427° C. (800° F.) (except where otherwise noted), a pressure of 1825 kPa (250 psig) and a WHSV of 5.

Analyses of reaction products were conducted at 4 and at 24 hours. The results of the conversions are set forth in Table XII as follows:

TABLE XII
RESULTS OF CATALYTIC DISPROPORTIONATION OF TOLUENE WITH MESITYLINE

Time on Stream: 4 hours

| Zeolite | Mesitylene Conversion, % | Toluene Conversion, % | Alkyl Group Selectivity, % | Ring Conversion, % | Xylene/Benzene Mole Ratio |
|---|---|---|---|---|---|
| 1 wt. % Ni-ZSM-5 | 43.3 | 27.0 | 93.7 | 98.6 | 4.17 |
| ZSM-5 | 59.2 | 39.8 | 86.6 | 100.7 | 1.96 |
| Steamed ZSM-5 | 43.6 | 43.5 | 93.5 | 99.1 | 2.44 |
| Steamed Beta | 61.5 | 35.6 | 94.3 | 99.8 | 7.14 |
| Steamed 0.1 wt. % Pt-Beta | 60.5 | 41.6 | 94.7 | 97.8 | 7.69 |

Time on Stream: 24 hours

| Zeolite | Mesitylene Conversion, % | Toluene Conversion, % | Alkyl Group Selectivity, % | Ring Conversion, % | Xylene/Benzene Mole Ratio |
|---|---|---|---|---|---|
| 1 wt. % Ni-ZSM-5 | 42.5 | 28.2 | 94.2 | 98.7 | 4.00 |
| ZSM-5 | — | — | — | — | — |
| Steamed ZSM-5 | 37.5 | 44.0 | 93.9 | 99.0 | 2.13 |
| Steamed Beta | 57.1 | 27.4 | 94.2 | 100.3 | 9.09 |
| Steamed 0.1 wt. % Pt-Beta | 60.8 | 37.5 | 94.4 | 98.4 | 8.33 |

These data show that the zeolite Beta catalyst compositions were more active, more stable and more selective (formation of more xylene than benzene) than the ZSM-5 catalyst compositions. The addition of 0.1% platinum to the Beta catalyst composition further improved stability while maintaining the noted advantage in the xylene/benzene mole ratios.

EXAMPLES 20-22

These examples compare the performance of two catalysts the use of which is within the scope of the invention, i.e. 0.1 wt. % Pt-zeolite Beta (Example 20) and 0.1 wt. % Pt-ZSM-12 (Example 22), with a zeolite the use of which is outside the scope of the invention, i.e. 0.1 wt. % Pt-mordenite (Example 21). Each catalyst composition contained 65% of the zeolite and 35% Kaiser alumina. The catalysts were steamed for 10 hours at 540° C. (1000° F.) for the zeolite Beta and 4 hours at 480° C. (900° F.) for the mordenite and ZSM-12 at atmospheric pressure and 100% steam. These steaming conditions provide catalysts having Alpha Values of approximately 50 prior to impregnation with platinum. The platinum was incorporated in each steamed catalyst by the incipient wetness technique using chloroplatinic acid.

Analysis of the $C_9+$ aromatic feed employed in these examples is set forth below in Table XIII as follows:

TABLE XIII

| $C_9+$ Aromatics Feed Composition | |
|---|---|
| Component | Wt. % |
| Xylene | 0.26 |
| Trimethylene | 38.78 |
| Ethyltoluene | 37.59 |
| Propylbenzene | 5.70 |
| Di-ethylbenzene | 5.72 |
| Di-methylethylbenzene | 4.65 |
| Total $C_9$ Aromatics | 83.39 |
| Total $C_{10}$ Aromatics | 14.36 |
| Total Aromatics | 99.34 |
| Total Non-Aromatics | 0.00 |

Four feedstocks were evaluated: a 60/40 wt. % toluene/$C_9+$ aromatics blend (Feedstock A), a 40/60 wt. % toluene/$C_9+$ aromatics blend (Feedstock B), the $C_9+$ aromatics feed by itself (Feedstock C) and the $C_9+$ aromatics feed containing 10 wt. % n-decene (Feedstock D). The results obtained with each of the three catalyst compositions and each of the foregoing feedstocks are summarized in Table XIV as follows:

TABLE XIV

| | Example 20 | Exaxple 21 | Example 22 |
|---|---|---|---|
| Feedstock A, % Conversion | | | |
| Trimethylbenzene | 62 | 57 | 54 |
| Ethyltoluene | 55 | 68 | 70 |
| $C_{10}$ Aromatics | 37 | 49 | 39 |
| Xylene/Benzene Mole Ratio | 2.86 | 1.96 | 1.79 |
| Feedstock B, % Conversion | | | |
| Trimethylbenzene | 53 | 52 | 58 |
| Ethyltoluene | 51 | 55 | 68 |
| $C_{10}$ Aromatics | 15 | 35 | 31 |
| Xylene/Benzene Mole Ratio | 3.85 | 3.03 | 2.70 |
| Feedstock C, % Conversion | | | |
| Trimethylbenzene | 44 | 40 | 52 |
| Ethyltoluene | 66 | 66 | 77 |
| $C_{10}$ Aromatics | <1 | 31 | 31 |
| Xylene/Benzene Mole Ratio | 5.88 | 5.26 | 6.67 |
| Feedstock D, % Conversion | | | |
| Trimethylbenzene | 21 | 34 | 34 |
| Ethyltoluene | 42 | 56 | 68 |
| $C_{10}$ Aromatics | — | 9 | 17 |
| Xylene/Benzene Mole Ratio | 2.86 | 4.55 | 5.88 |

In each example, 10 cc. of catalyst composition crushed to 20/60 mesh was introduced into a stainless steel reactor which was then heated to constant reaction temperature 427° C. and pressure 1825 kPa in flowing hydrogen. The hydrocarbon feed, i.e. toluene and the foregoing $C_9+$ aromatic, was started (WHSV=2.5) and material balances were taken after 48 hours onstream.

Zeolite Beta (Example 20) exhibited the highest transalkylation selectivity, i.e. the highest xylene/benzene mole ratio (Feedstocks A and B) of the three catalysts. While mordenite (Example 21) and ZSM-12 (Example 22) performed about the same in the disproportionation of toluene (Feedstocks A and B), as the amount of $C_9+$ aromatics in the feedstock increased (Feedstock B), the ZSM-12 catalyst performed significantly better. Although each catalyst experienced a reduction in activity upon the addition of paraffin, i.e. n-decene (Feedstock D), ZSM-12 (Example 22) was least affected indicating that this zeolite is especially desirable for the transalkylation/disproportionation conversion of $C_9+$ aromatic-containing feeds which have not been previously processed for the removal of paraffin.

What is claimed is:

1. A process for converting a feedstock containing at least one C9+ aromatic compound to a product containing C6-C8 aromatic compounds which comprises contacting said feedstock at conversion conditions with a catalyst comprising a zeolite characterized by an X-ray diffraction pattern including values set forth in Table I of the specification.

2. The process of claim 1 wherein the zeolite is MCM-22.

3. The process of claim 1 wherein the zeolite is characterized by an X-ray diffraction pattern including values set forth in Table II of the specification.

4. The process of claim 1 wherein the zeolite has equilibrium adsorption capacities greater than 4.5 wt. % for cyclohexane vapor and greater than 10 wt. % for n-hexane vapor.

5. The process of claim 1 wherein the zeolite has a composition comprising the molar relationship

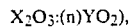

$X_2O_3:(n)YO_2$, wherein n is at least 10, X is a trivalent element and Y is a tetravalent element.

6. The process of claim 5 wherein X is selected from the group consisting of aluminum, boron, gallium and combinations thereof and Y is selected from the group consisting of silicon, germanium and combination thereof.

7. The process of claim 5 wherein X comprises aluminum and Y comprises silicon.

8. The process of claim 1 wherein the zeolite has been treated to replace original cations, at least in part, with a cation or mixture of cations, or to otherwise acquire a cation or mixture of cations, selected from the group consisting of hydrogen, hydrogen precursors, rare earth metals, and metals of Groups IIA, IIIA, IVA, IB, IIB, IIIB, IVB, VIB and VIII of the Periodic Table.

9. The process of claim 1 wherein the zeolite has been thermally treated at a temperature up to about 925° C. in the presence or absence of steam.

10. The process of claim 8 wherein the zeolite has been thermally treated at a temperature up to about 925° C. in the presence or absence of steam.

11. The process of claim 1 wherein the C9+ aromatics represent at least about 3 wt % of the total feedstock, the balance of the feedstock comprising benzene, toluene, or a mixture thereof.

12. The process of claim 1 wherein C9+ aromatics represent from about 10 to about 70 wt % of the total feedstock, the balance of the feedstock comprising benzene, toluene or a mixture thereof.

13. The process of claim 1 wherein the conversion conditions include a temperature of from about 600° F. to about 1100° F., a pressure of from atmospheric to about 1000 psig and a hydrogen to hydrocarbon mole ratio of from 0 to about 10.

14. The process of claim 1 wherein the zeolite possesses a Constraint Index of from 1 to about 2.5.

15. The process of claim 1 wherein the product comprises xylenes and benzene in a xylenes/benzene mole ratio of greater than about 0.8.

16. A process for converting feedstock containing at least one C9+ aromatic compound to a product containing C6-C8 aromatic compounds which comprises contacting said feedstock at conversion conditions with a catalyst composition comprising zeolite beta wherein said zeolite beta has been steamed to reduce acidity.

* * * * *